(12) United States Patent
Martin et al.

(10) Patent No.: US 8,966,740 B2
(45) Date of Patent: Mar. 3, 2015

(54) JOINED INFLATION PORTIONS FOR BIFURCATION CATHETER

(75) Inventors: Daryl L. Martin, Maple Grove, MN (US); Richard A. Noddin, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 155 days.

(21) Appl. No.: 13/439,632

(22) Filed: Apr. 4, 2012

(65) Prior Publication Data

US 2012/0186064 A1 Jul. 26, 2012

Related U.S. Application Data

(62) Division of application No. 12/121,110, filed on May 15, 2008, now abandoned.

(51) Int. Cl.
| | |
|---|---|
| B23P 25/00 | (2006.01) |
| A61F 2/856 | (2013.01) |
| A61F 2/958 | (2013.01) |
| A61F 2/954 | (2013.01) |

(52) U.S. Cl.
CPC ............ *A61F 2/856* (2013.01); *A61F 2/958* (2013.01); *A61F 2/954* (2013.01)
USPC ...................................... 29/527.1

(58) Field of Classification Search
CPC ......... A61F 2/958; A61F 2/954; A61F 2/856; A61F 2/915; A61F 2002/061; A61F 2002/9155; A61M 2025/1045; A61M 25/1029; A61M 25/0009
USPC .......... 29/421.1, 527.1, 447; 604/284, 96.01; 606/194; 623/1.35; 264/299, 918, 550, 264/151, 267, 292, 320, 325
See application file for complete search history.

(56) References Cited

U.S. PATENT DOCUMENTS

| | | | | |
|---|---|---|---|---|
| 4,050,667 | A | * | 9/1977 | Kossett ........................ 249/82 |
| 5,304,198 | A | | 4/1994 | Samson |
| 5,437,632 | A | | 8/1995 | Engelson |
| 5,720,735 | A | | 2/1998 | Dorros |
| 5,792,105 | A | | 8/1998 | Lin |
| 6,099,497 | A | | 8/2000 | Adams et al. |
| 6,117,117 | A | * | 9/2000 | Mauch ......................... 604/284 |

(Continued)

FOREIGN PATENT DOCUMENTS

| | | |
|---|---|---|
| EP | 0705116 | 4/1996 |
| WO | 0044307 | 8/2000 |

(Continued)

OTHER PUBLICATIONS

U.S. Appl. No. 60/776,149 to Andrzej Malewicz, filed Feb. 22, 2006.

*Primary Examiner* — Moshe Wilensky
(74) *Attorney, Agent, or Firm* — Seager, Tufte & Wickhem LLC

(57) ABSTRACT

An example multi-lumen member forming dual inflation portions of a catheter assembly for treating bifurcated vessels includes a main tube defining a main lumen and a main inflation portion. The member includes a side tube defining a side lumen and a side inflation portion, the side tube extending along at least a first length of the main tube. The member also includes a portion extending along the first length of the main tube and coupling the main tube to the side tube to form a dual lumen configuration.

10 Claims, 4 Drawing Sheets

(56) References Cited

U.S. PATENT DOCUMENTS

| | | | |
|---|---|---|---|
| 6,142,973 A * | 11/2000 | Carleton et al. | 604/96.01 |
| 6,146,356 A | 11/2000 | Wang | |
| 6,168,748 B1 * | 1/2001 | Wang et al. | 264/520 |
| 6,210,380 B1 * | 4/2001 | Mauch | 604/284 |
| 6,210,429 B1 | 4/2001 | Vardi | |
| 6,231,543 B1 | 5/2001 | Hedge et al. | |
| 6,261,273 B1 | 7/2001 | Ruiz | |
| 6,290,265 B1 * | 9/2001 | Warburton-Pitt et al. | 285/131.1 |
| 6,325,826 B1 | 12/2001 | Vardi | |
| 6,635,214 B2 * | 10/2003 | Rapacki et al. | 264/250 |
| 6,692,483 B2 | 2/2004 | Vardi | |
| 6,706,062 B2 | 3/2004 | Vardi | |
| 6,802,856 B2 * | 10/2004 | Wilson | 623/1.11 |
| 6,863,757 B1 * | 3/2005 | Gonzalez et al. | 156/86 |
| 8,088,102 B2 * | 1/2012 | Adams et al. | 604/96.01 |
| 8,556,955 B2 * | 10/2013 | Gregorich et al. | 623/1.11 |
| 2001/0004706 A1 | 6/2001 | Hojeibane | |
| 2002/0111675 A1 * | 8/2002 | Wilson | 623/1.35 |
| 2002/0183826 A1 * | 12/2002 | Dorn et al. | 623/1.11 |
| 2003/0097169 A1 * | 5/2003 | Brucker et al. | 623/1.11 |
| 2004/0138737 A1 | 7/2004 | Davidson | |
| 2004/0176837 A1 | 9/2004 | Atladottir | |
| 2005/0015108 A1 | 1/2005 | Williams et al. | |
| 2005/0085845 A1 | 4/2005 | Hilaire | |
| 2005/0102019 A1 * | 5/2005 | Yadin | 623/1.11 |
| 2005/0192656 A1 | 9/2005 | Eidenschink | |
| 2006/0074476 A1 * | 4/2006 | Holman et al. | 623/1.11 |
| 2007/0032855 A1 | 2/2007 | Davidson et al. | |
| 2007/0267780 A1 * | 11/2007 | Schewe et al. | 264/299 |
| 2008/0171975 A1 | 7/2008 | Jennings et al. | |
| 2009/0036830 A1 | 2/2009 | Jablonski et al. | |
| 2009/0292241 A1 * | 11/2009 | von Oepen et al. | 604/96.01 |
| 2013/0026681 A1 * | 1/2013 | Kleiner et al. | 264/458 |

FOREIGN PATENT DOCUMENTS

| | | |
|---|---|---|
| WO | 0209618 | 2/2002 |
| WO | 2006113838 | 10/2006 |

* cited by examiner

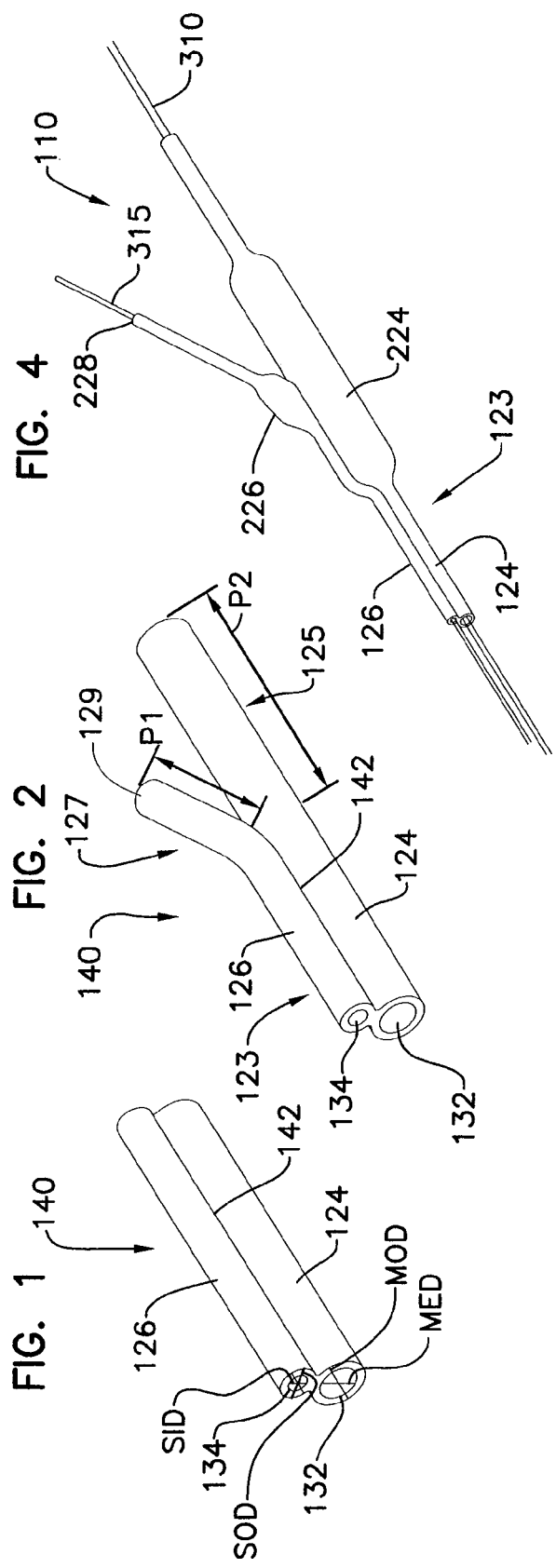
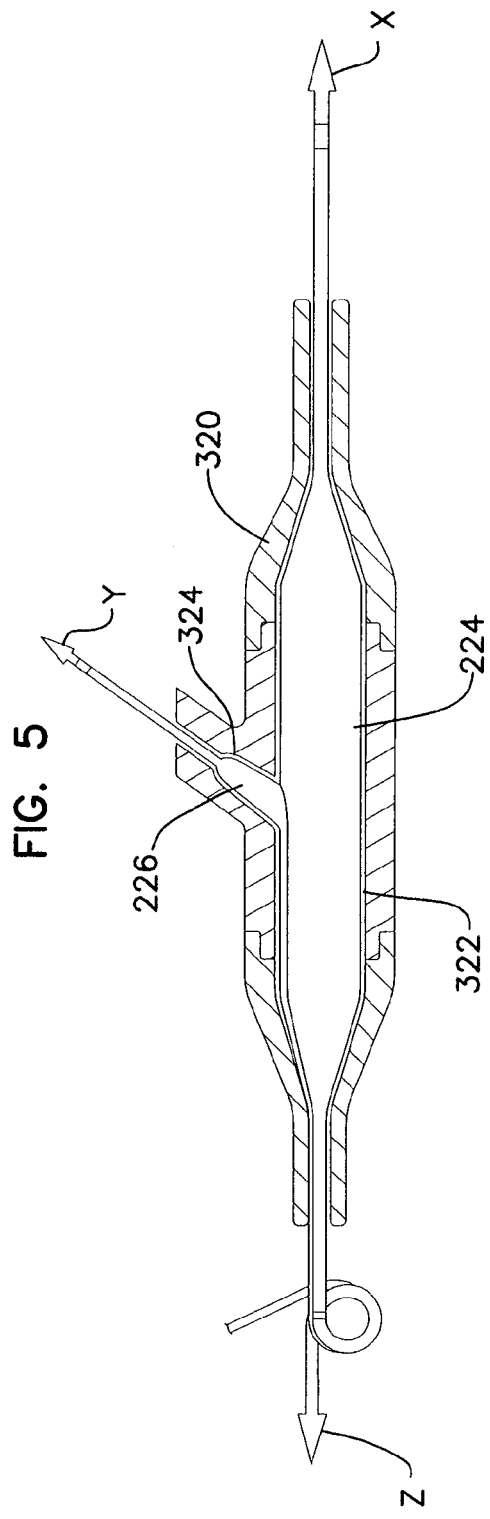

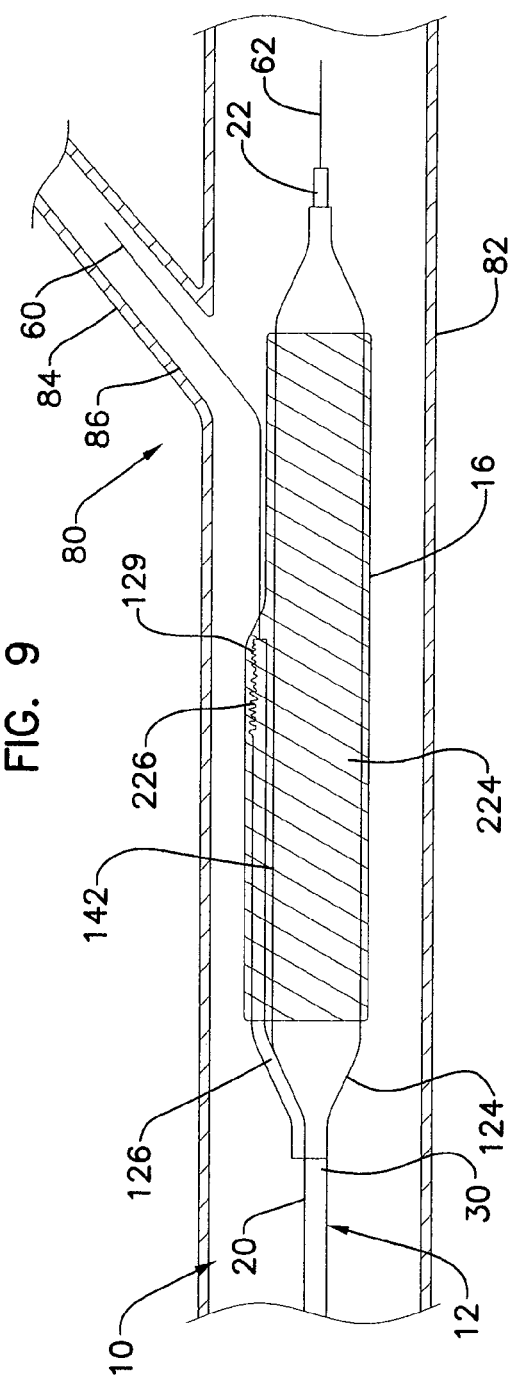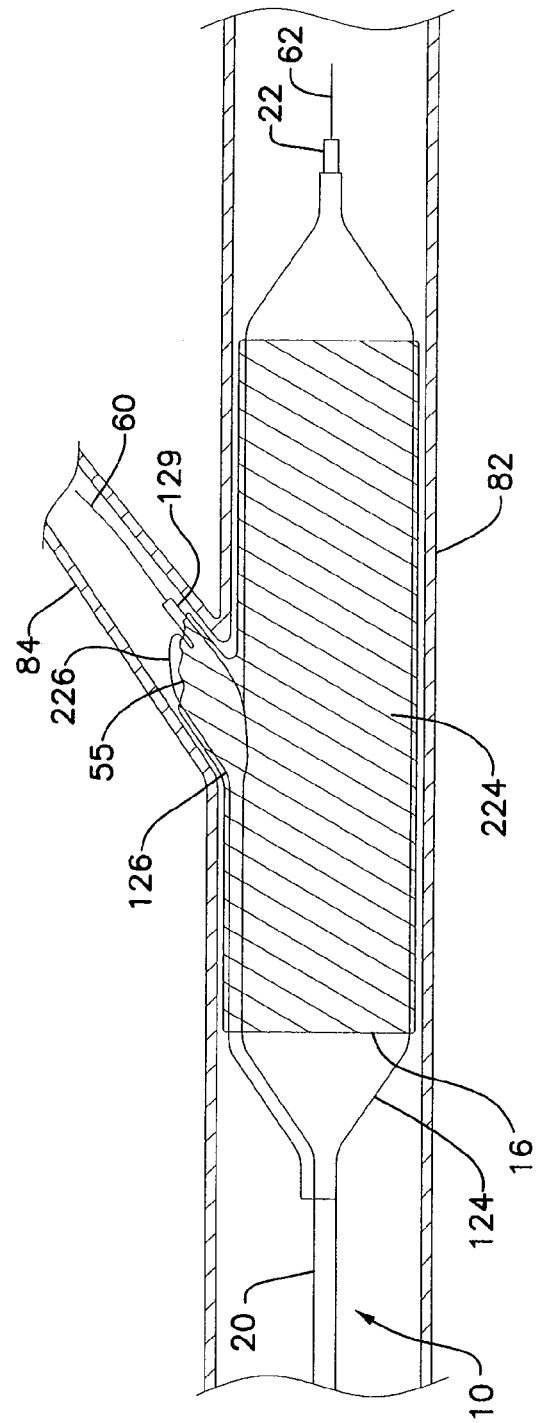

JOINED INFLATION PORTIONS FOR BIFURCATION CATHETER

RELATED APPLICATIONS

This application is a divisional of co-pending U.S. application Ser. No. 12/121,110, filed May 15, 2008, the entire disclosure of which is incorporated herein by reference.

TECHNICAL FIELD

This disclosure relates to catheter systems and methods for treating vessel bifurcations.

BACKGROUND

Catheters are used with stents and balloon inflatable structures to treat strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular body organ for treating conditions such as, for example, occlusions, stenoses, aneurysms, dissection, or weakened, diseased, or abnormally dilated vessel or vessel wall, by expanding the vessel or by reinforcing the vessel wall. Once delivered, the stents can be expanded using one or more inflation members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed.

SUMMARY

The present disclosure relates generally to catheter assemblies for treatment of bifurcated lumens in a patient, such as vessel bifurcations.

In one arrangement, a catheter assembly includes main and side balloons that are formed by joined tubes of a two-lumen member. The tubes of the member form a main tube and a side tube that are joined at a portion along at least a portion of their lengths. The side tube is separated from the main tube along a portion of the portion thereof, while the remaining portions of the side tube and main tube remain joined. In this configuration, the main and side balloons can be formed from the main and side tubes.

There is no requirement that an arrangement or method include all features characterized herein to obtain some advantage according to this disclosure.

DESCRIPTION OF THE DRAWINGS

FIG. 1 is a schematic side perspective view of an example two-lumen tube precursor for forming main and side balloons of a catheter assembly for treatment of a vessel bifurcation.

FIG. 2 is a schematic side perspective view of the two-lumen tube precursor of FIG. 1 with a portion of the side tube separated from a portion of the main tube.

FIG. 4 is a schematic side perspective view of the two-lumen tube precursor of FIG. 2 with two example mandrels inserted therein.

FIG. 5 is a schematic side view of the two-lumen tube precursor of FIG. 2 inserted into an example three-piece composite mold.

FIG. 9 is a schematic side view of an example catheter assembly for treatment of a vessel bifurcation in a position prepared for treatment of a vessel bifurcation.

FIG. 10 is a schematic side view of the catheter assembly shown in FIG. 9 with the side and main balloons inflated and the stent expanded at the vessel bifurcation.

DETAILED DESCRIPTION

Figure 3:
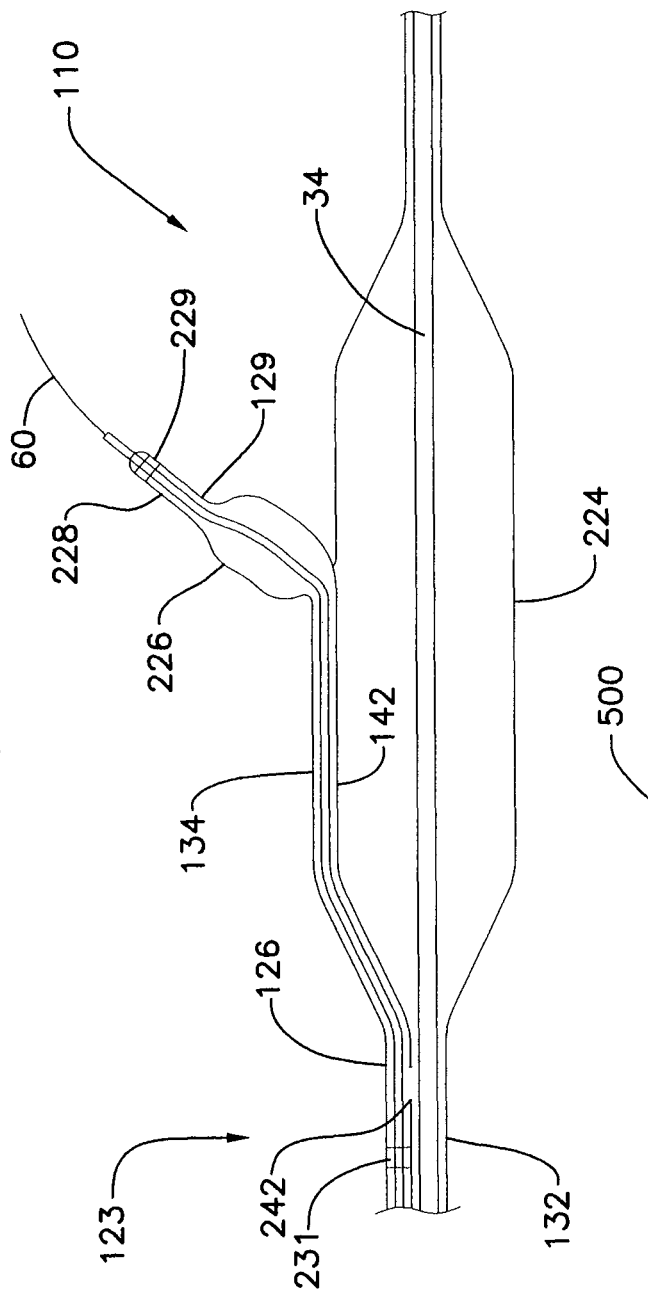
FIG. 3 is a schematic side view of the main and side tubes of FIG. 2 with inflation portions formed therein.

This disclosure relates to bifurcation treatment systems, catheter assemblies, and related methods of treating bifurcations in a patient's body. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other; and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively, that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the principles disclosed herein include cardiac, coronary, renal, peripheral vascular, gastrointestinal, pulmonary, urinary, and neurovascular systems. The catheter assemblies, systems and methods disclosed herein can be used for locating a branch vessel of the vessel bifurcation and for placement of a stent relative to the vessel bifurcation for treatment of the vessel bifurcation.

The example catheter assemblies disclosed herein include, at a distal end portion thereof, a main catheter branch and a side catheter branch. The side catheter branch typically includes a side guidewire housing that defines a side guidewire lumen. A distal end portion of the side catheter branch is configured to extend into a branch vessel at a vessel bifurcation. The side catheter branch is used to align features of a stent carried by the proximal end portion of the vessel bifurcation treatment system with an ostium (also referred to as a branch vessel opening) into the branch vessel.

The main catheter branch includes a catheter shaft having a distal end portion. A main balloon and a side balloon (sometimes referred to as main and side inflation portions) are positioned at the distal end portion of the catheter shaft. A main catheter branch includes a main guidewire housing that defines a main guidewire lumen. A distal waist portion of the main balloon is operably mounted to the main guidewire housing. A proximal waist portion of the main balloon is operably mounted to the distal end portion of the catheter shaft.

The side balloon is positioned on a side inflation member that extends generally in parallel with the main balloon. The side inflation member defines a side inflation lumen. The side inflation member includes proximal and distal segments that are connected in fluid communication with the side balloon. The distal and proximal segments of the side inflation member can alternatively be considered elongate waist portions of the side balloon that extend in the distal and proximal directions, respectively.

The waist portion of a balloon is typically at one of the opposing ends of the balloon. The waist portion is used to secure or otherwise mount the balloon to a mounting surface, such as the outer surface of a shaft. Some example mounting surfaces for the waist portions of a main balloon are the outer surface of a distal end portion of a catheter shaft and the outer surface of a main guidewire housing. The waist portion is typically configured to not expand in size when the balloon is inflated with inflation fluid. In many instances a balloon is formed by molding from a length of tubular structure (e.g., a polymeric catheter shaft). The portions of the tubular structure extending on opposite sides of the molded balloon can be considered waist portions of the balloon regardless of the length of the waist portions.

Referring now to FIGS. 1-3, an example two-lumen balloon system 110 is shown. The two-lumen balloon system 110 includes a main tube 124 and a side tube 126.

In the example shown, the main tube 124 and the side tube 126 are formed of a single two-lumen tube precursor 140 (sometimes referred to herein as a "multi-lumen member"). The precursor 140 is an integrated structure that defines two lumens and from which at least two inflation portions are formed. For example, the main tube 124 of precursor 140 is used to form a main balloon and associated waist portions for a catheter assembly, and the side tube 126 is used to form a side balloon and associated waist portions for the catheter assembly.

In the arrangement show, the main tube 124 is larger in cross-sectional area and defines a larger main inflation lumen 132, and the side tube 126 is smaller in cross-sectional area and defines a smaller side inflation lumen 134. In one example, a largest main inner dimension MID for the main inflation lumen 132 is preferably 0.39 to 0.64 mm, more preferably 0.49 to 0.54 mm, and most preferably 0.52 mm, and a largest main outer dimension MOD for the main tube 124 is preferably 0.75 to 1.00 mm, more preferably 0.85 to 0.90 mm, and most preferably 0.88 mm. A largest side inner dimension SID for the side inflation lumen 134 is preferably 0.25 to 0.60 mm, more preferably 0.35 to 0.50 mm, and most preferably 0.40 mm, and the side largest outer dimension SOD for the side tube 126 is preferably 0.60 to 0.90 mm, more preferably 0.70 to 0.80 mm, and most preferably 0.73 mm. In alternative embodiments, other dimensions can be used.

The main tube 124 and the side tube 126 of the precursor 140 are joined at a continuous portion 142 extending along at least a portion of the length of the main and side tubes 124, 126. The portion 142 is located at the surface at which the main tube 124 is connected to the side tube 126. The portion 142 can extend longitudinally along an entire portion of the main and side tubes 124, 126, or only along a portion of the main and side tubes 124, 126.

In the example shown, the main tube 124 and the side tube 126 of the precursor 140 form two generally circular shapes that are connected at the portion 142. In one example, the main and side tubes 124, 126 form a dual lumen configuration. The configuration can, in embodiments, have a generally two lumen waisted shape or a generally figure eight ("8") cross-section. Other configurations, such as a generally round or oval cross-section for the precursor 140, can also be used.

In one example, the main tube 124 and the side tube 126 are joined as the precursor 140 is manufactured, as described below. In another example, the main tube 124 and the side tube 126 can be made separately, and are then be joined using an adhesive or other coupling process.

In example embodiments, the portion 142 is integrally formed with the main and side tubes 124, 126 such that the portion 142 is continuously coupled to the main and side tubes 124, 126. For example, the two-lumen tube precursor 140 can be extruded, so that the main tube 124 and the side tube 126 of the precursor 140 form a single integrated unit. In other examples, the main and side tubes 124, 126 are formed separately and coupled (e.g., by welding or other techniques) to one another along a continuous length to form the portion 142.

In one arrangement, the precursor 140 is formed by extrusion of a highly crystalline polymeric material such as Nylon 12 or PEBAX®. In some alternatives, a multi-layered tube including multiple materials can be used. Other materials, such as those listed below, and methods can also be used to form the two-lumen tube precursor 140 by, for example, including varying ratios of materials depending on material combination and performance requirements.

As shown in FIG. 2, a distal portion 127 of the side tube 126 can be separated from a distal portion 125 of the main tube 124. This separation can be realized prior to the two-lumen tube precursor 140 being molded to form the inflation portions (e.g., inflation portions 224, 226) of the main tube 124 and the side tube 126.

For example, the distal portion 127 of the side tube 126 is separated from the distal portion 125 of the main tube 124 by breaking, cutting, or otherwise severing a portion of the portion 142 formed between the main tube 124 and the side tube 126. In some arrangements, the portion 142 can be severed by cutting the portion 142 using a mechanical device such as a knife or a laser (e.g., an ultraviolet "UV" ablation laser).

In this manner, a length P1 of the distal portion 127 of the side tube 126 and a length P2 of the distal portion 125 of the main tube 124 can be tailored to specific applications. In one example, the lengths P1 and P2 are greater than that needed for use and can be trimmed during assembly. For example, the lengths P1 and P2 can be greater than 5 or 6 inches and can be trimmed to a desired length.

The lengths P1, P2 of the main and side tubes 124, 126 can be modified by cutting one or both of the tubes 124, 126 to the desired length. In certain arrangements, the length P1 of the distal portion 127 of the side balloon is increased to provide reduced distal crimped profiles and pre-dilation capabilities. Such an arrangement also allows for enhanced side branch alignment prior to complete main branch or ostial stent deployment. Shorter lengths P1 also contribute to decreased distal crimped profiles.

Figure 7:
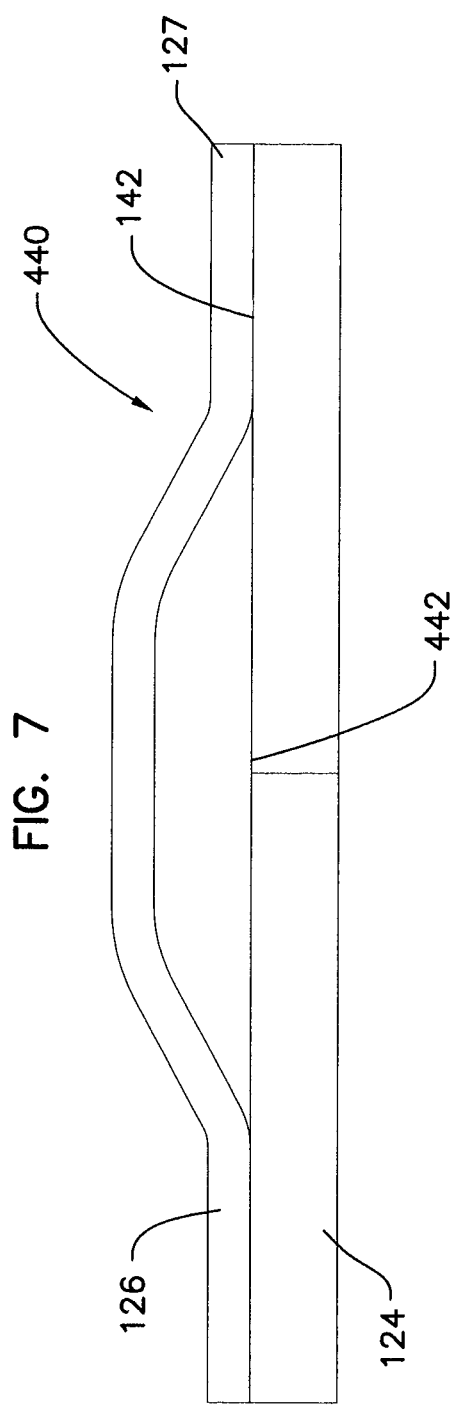
FIG. 7 is a schematic side view of another example two-lumen tube precursor for forming main and side balloons of a catheter assembly for treatment of a vessel bifurcation.
Figure 8:
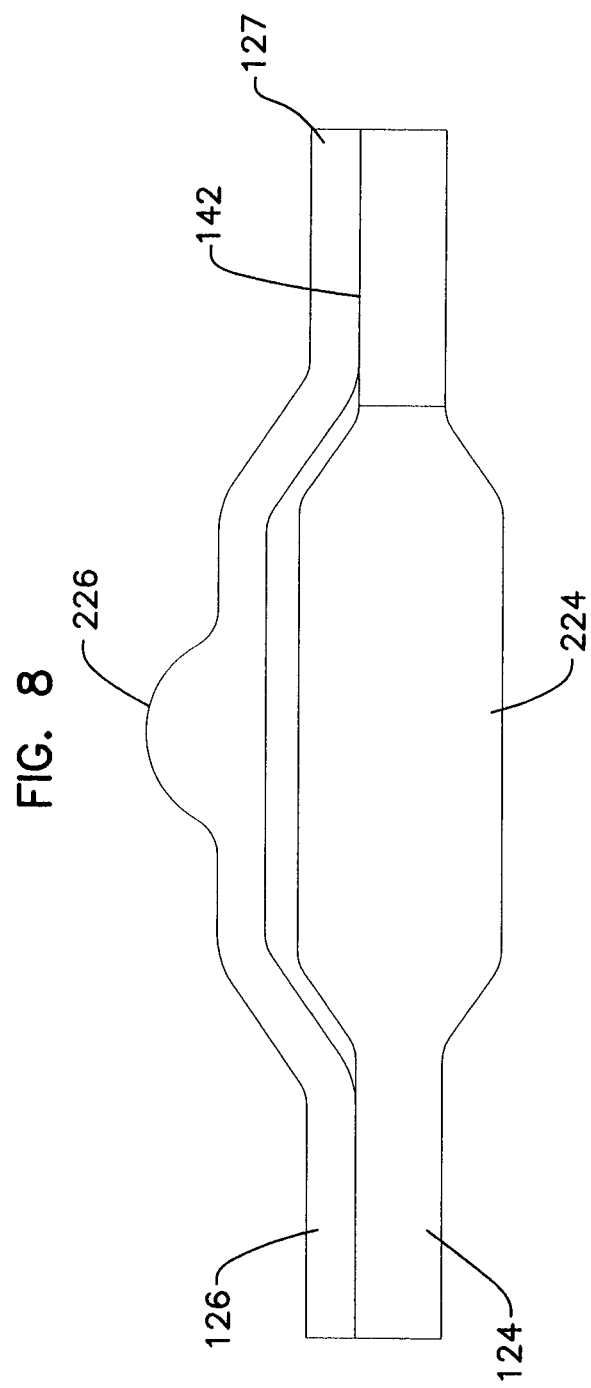
FIG. 8 is a schematic side view of the two-lumen tube precursor of FIG. 7 with a portion of the side balloon separated from a portion of the main balloon.

A distal waist 129 of the distal portion 127 of the side tube 126 can be allowed to remain free, as shown in FIGS. 1-3, or can be attached to a distal tip of the catheter system, as shown in FIGS. 7 and 8, described below.

Figure 6:
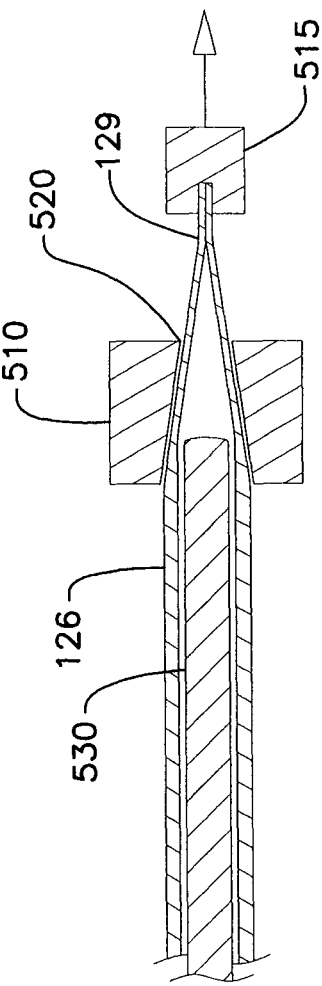
FIG. 6 is a schematic cross-sectional side view of the distal end portion of the two-lumen tube precursor of FIG. 2 inserted into a skive member.

Referring now to FIGS. 4-6, mandrels 310, 315 can be heated to generally form the inflation portions 224, 226 of the main and side tubes 124, 126, respectively. Once formed, the mandrels 310, 315 are removed, and the main and side tubes 124, 126 of the precursor 140 are placed into a three-piece composite mold 320, as shown in FIG. 5. In one example, the mold 320 is a three-piece mold such as that shown herein. In other embodiments, the mold 320 can be a two-piece "claim shell" type mold. Other configurations are possible.

The inflation portions 224, 226 of the main and side tubes 124, 126 are then inflated, and the main and side tubes 124, 126 are stretched by exerting forces in the X, Y, and Z directions. The mold 320 can also be heated prior to and/or during inflation of the inflation portions 224, 226. Finally, the main and side tubes 124, 126 are removed from the mold 320.

In the arrangement shown, the mold 320 forms a main balloon cavity 322 for forming inflation portion 224, and a side balloon cavity 324 for forming inflation portion 226. The shapes of the main and side balloon cavities 322, 324 can be modified to modify the resulting shapes of the inflation portions 224, 226. For example, the shape of the side balloon cavity 324 can be modified, as well as its position relative to the main balloon cavity 322, to change the shape and position of inflation portion 226 relative to inflation portion 224.

Referring to FIG. 6, the distal waist 129 of the side tube 126 is further tapered using a skive member 500 including a mandrel 530 positioned in the side tube 126, and a second member 510 including a tapering aperture 520 formed therein. The distal waist 129 is pulled through the tapering aperture 520 of the second member 510 to further taper the distal waist 129, and a holding member 515 is attached to the distal waist 129. In example embodiments, the tapering aperture 520 can be heated to soften the material.

Once the formation of the inflation portions 224, 226 of the tubes 124, 126 are complete, the main and side tubes 124, 126 are bonded to the catheter shaft (e.g., catheter distal portion 30 of shaft 20). Since the main and side tubes 124, 126 are already coupled to each other at proximal end 123, it is not necessary to bond the main and side tubes 124, 126. In this manner, less bonding is required to couple the balloon system 110 to the catheter shaft, and a more robust connection between the main and side tubes 124, 126 and the catheter shaft is accomplished.

In the arrangement shown, the main lumen 132 and the side lumen 134 are in fluid communication through a port 242 (see FIG. 3) formed therebetween. In this manner, fluid is delivered through the main lumen 132 and the side lumen 134 to inflate inflation portions 224, 226 of the main and side tubes 124, 126, respectively.

In one example, a distal end 228 of the distal waist 129 of the side tube 126 includes an elastomeric sealable bushing 229. The bushing 229 seals the side inflation lumen 134 with respect to a branch vessel guidewire (e.g., guidewire 60) extending through the side tube 126. In some arrangements, another bushing 231 is located downstream of the port 242 to seal the other end of the side inflation lumen 134. With the branch vessel guidewire in place through the side tube 126, bushings 229, 231 seal against the guidewire to allow the inflation portion 226 of the side tube 126 to be inflated. Once the guidewire is removed from the bushings 229, 231 (e.g., during removal), the seals between one or both of the bushings 229, 231 and the guidewire is broken to allow the side tube 126 to deflate by releasing the stored inflation fluid into the vessel. Alternative designs are possible. For example, in one arrangement, the main and side inflation lumens 132, 134 are separate, and fluid is delivered separately through inflation lumens 132, 134 to inflatable portions 224, 226. In yet another arrangement, the distal end 228 of the side tube 126 is plugged, or attached to the distal tip of the catheter system (see FIGS. 7 and 8).

Referring now to FIGS. 7 and 8, another example two-lumen tube precursor 440 is shown including the main and side tubes 124, 126. For precursor 440, the portion 142 formed between the main and side tubes 124, 126 is severed at a midportion 442 between the main and side tubes 124, 126, so that the distal portion 127 of the side tube 126 remains attached to the main tube 124 through the portion 142. The inflation portions 224, 226 of the main and side tubes 124, 126 can then be formed in the tube precursor 440 in a manner similar to that described above.

An example catheter assembly 10 is shown schematically with reference to FIGS. 9 and 10. The catheter assembly 10 is configured for treatment of a vessel bifurcation, such as a vessel bifurcation 80. The catheter assembly 10 includes a main catheter branch 12. The main catheter branch 12 includes a catheter shaft 20 having a distal end portion 30. The catheter shaft 20 defines a main inflation lumen, and includes a main guidewire housing 22 defining a main guidewire lumen (not shown).

The assembly 10 also includes a stent 16 surrounding the balloon system 110 shown in FIGS. 1-3. The balloon system 110 is coupled to the distal end portion 30 of the catheter shaft 20. When uninflated, as shown in FIG. 9, the inflation portions 224, 226 of the main and side lumens 124, 126 maintain a generally collapsed profile. When inflated, as shown in FIG. 10, the inflation portions 224, 226 of the main and side lumens 124, 126 extend radially outward relative to the longitudinal axis of the assembly 10.

The catheter assembly 10 can be used for treatment of the vessel bifurcation 80. Typically, a main vessel guidewire 62 is inserted into a main vessel 82 of the vessel bifurcation 80 to a point distal of the vessel bifurcation 80. A branch vessel guidewire 60 is advanced to the vessel bifurcation 80 and inserted through an ostium or opening 86 of a branch vessel 84. The catheter assembly 10 is advanced over the guidewires 60, 62 to the vessel bifurcation. The catheter assembly 10 is then advanced further distally until the distal waist 129 of the distal portion 127 of the side tube 126 is positioned within the branch vessel 84.

After proper positioning of the catheter assembly 10 is confirmed (using for example, a marker system as described below), the main and side inflation portions 224, 226 are inflated. Typically, inflation of the side inflation portion 226 can also result in expansion of a lateral branch expandable structure 55 surrounding a lateral branch opening of the stent 16. The expanded expandable structure 55 can extend through the ostium 86 and at least partially into the branch vessel 84.

The particular method steps described above can be altered in other example treatment methods. For example, one of the guidewires 60, 62 can be advanced with the catheter assembly 10 to the vessel bifurcation 80. In another example, the inflation portions 224, 226 can be inflated sequentially, rather than simultaneously, for purposes of, for example, improving alignment of the expandable structure 55 with the ostium 86 into the branch vessel 84.

A marker system can be used to help confirm proper radial and axial alignment of the expandable structure 55 of the stent 16 relative to the ostium 86 into the branch vessel 84. For example, the catheter assembly 10 can include marker material that is visible under X-ray or in fluoroscopy procedures. Any features of the assembly 10 that include marker material are more easily identified and distinguished under X-ray or in fluoroscopy procedures. Some example marker materials include gold, platinum and tungsten. In one embodiment, the marker material can be included in a band structure that is secured to one or more structures of the catheter assembly 10.

In other embodiments, the marker material is part of the material composition of portions of the catheter assembly 10. Viewability of features of the catheter assembly 10 under X-ray or fluoroscopy can assist the physician operating the assembly 10 to more easily adjust a position of the assembly 10 relative to the vessel bifurcation 80. Example markers and marker materials suitable for use with the assembly 10 are described in U.S. Pat. No. 6,692,483 to Vardi, et al., and co-pending U.S. Provisional Patent Application Ser. No. 60/776,149, filed on Feb. 22, 2006, and titled MARKER ARRANGEMENT FOR BIFURCATION CATHETER, which patent matters are incorporated herein by reference.

Alternative catheter assemblies to those described above are configured for use with stents having self-expanding features. Self-expanding stents and self-expanding features of a stent typically do not require the use of an inflatable member such as a balloon to expand the sent or stent feature. Typically, self-expanding stents, such as those stents described in U.S. Published Patent Application No. 2004/0176837, are held in a constricted state using a sheath that fits over the stent. In the constricted state, the stent is able to navigate through a body lumen to the treatment site. Once the stent and sheath are positioned at the treatment side, the sheath is retracted proximally to release the stent for expansion of the stent into a radially expanded state.

A wide variety of stents, catheters, and guidewire configurations can be used with the catheter assembly embodiments of the present disclosure. The inventive principles disclosed herein should not be limited to any particular design or configuration. Some example stents that can be used with the catheter assemblies disclosed herein can be found in, for example, U.S. Pat. Nos. 6,210,429, 6,325,826 and 6,706,062 to Vardi et al., co-pending U.S. patent application Ser. No. 10/644,550, filed on Aug. 21, 2003, and titled STENT WITH A PROTRUDING BRANCH PORTION FOR BIFURCATED VESSELS, and U.S. Published Patent Application No. 2004/0176837 titled SELF-EXPANDING STENT AND CATHETER ASSEMBLY AND METHOD FOR TREATING BIFURCATIONS, the entire contents of which are incorporated herein by reference. In general, the aforementioned stents include a lateral branch opening located between distal and proximal open ends of the stent. The lateral branch opening defines a path between an inner lumen of the stent and an area outside of the stent. The stent lateral branch opening is distinct from the cell openings defined between strut structures from which the stent sidewall is constructed. In some stents, the lateral branch opening can be surrounded by expandable structure. The expandable structure can be configured to extend radially into the branch lumen of the bifurcation upon expansion of, for example, an inflatable portion of the bifurcation treatment system. Typically, the stent is expanded after being positioned in the main lumen with the lateral branch opening aligned with an opening into the branch lumen. Alignment of the lateral branch opening with the opening into the branch lumen includes both radial and axial alignment. The stent, including the expandable structure surrounding the lateral branch opening, can be expanded with a single expansion or multiple expansions using one or more inflatable members.

A variety of alternative materials can be used for the catheter assembly 10. For example, the main and side lumens 124, 126 can be made of any suitable balloon material including compliant and non-compliant materials and combinations thereof. Some example materials for the balloons and catheters disclosed herein include thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyether-polyamide copolymers. One suitable material is Surlyn®, a copolymer polyolefin material (DuPont de Nemours, Wilmington, Del.). Still further suitable materials include thermoplastic polymers and thermoset polymeric materials, poly (ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Arkema, Philadelphia, Pa.). Other examples include nylons, such as aliphatic nylons, for example, Vestamid L21011F, Nylon 11 (Arkema), Nylon 6 (Honeywell), Nylon 6/10 (BASF), Nylon 6/12 (Ashley Polymers), or Nylon 12.

Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITELe (available from DSM, Erionspilla, Ind.), e.g., ARNITELe EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356, which is incorporated herein by reference.

As described herein, a multi-lumen member forming dual inflation portions of a catheter assembly for treating bifurcated vessels includes a main tube defining a main lumen and a main inflation portion, and a side tube defining a side lumen and a side inflation portion, the side tube extending along at least a first length of the main tube. The member also includes a portion extending along the first length of the main tube and coupling the main tube to the side tube to form a dual lumen configuration.

In another arrangement, a dual balloon system for a catheter assembly for deployment in a bifurcated vessel includes a main tube defining a main lumen and a main inflation portion, and a side tube defining a side lumen and a side inflation portion, the side tube extending along the main tube. The system also includes a portion coupling the main tube to the side tube to form a dual lumen configuration, wherein a distal portion of the portion is severed to separate a distal length of the side tube from the main tube.

In yet another arrangement, a method of forming a dual balloon system for a catheter assembly for deployment in a bifurcated vessel includes: extruding a multi-lumen member including a main tube and a side tube that are joined at a portion to form an integrated unit, the main tube defining a main lumen, and the side tube defining a side lumen; separating a distal portion of the side tube from the main tube at the portion; forming a main inflation portion in the main tube; and forming a side inflation portion in the side tube.

It is noted that not all of the features characterized herein need to be incorporated within a given arrangement, for the arrangement to include improvements according to the present disclosure.

What is claimed is:

1. A method of forming a dual balloon system for a catheter assembly for deployment in a bifurcated vessel, the method comprising:
   (a) extruding a multi-lumen member including a main tube and a side tube that are joined at a portion along a length of the main tube and the side tube to form an integrated unit, the main tube defining a main lumen, and the side tube defining a side lumen;
   (b) separating a middle portion of the side tube from the main tube at the joined portion such that the side tube is joined to and extends along at least a first length of the main tube proximal of the separated middle portion and is joined to and extends along at least a second length of the main tube distal to the separated middle portion;
   (c) forming a main inflation portion in the main tube;
   (d) forming a side inflation portion in the side tube; and
   (e) once the formation of the main and side inflation portions is complete, the method further comprises bonding the main and side tubes to a catheter shaft.

2. The method of claim 1, wherein (c) forming the main inflation portion and (d) forming the side inflation portion further comprises:
   (i) introducing a first mandrel into the main tube, and a second mandrel into the second tube; and
   (ii) heating the main tube and the side tube.

3. The method of claim 2, wherein (c) forming the main inflation portion and (d) forming the side inflation portion further comprises:
   (iii) placing the multi-lumen member into a mold;
   (iv) inflating the main inflation portion and the side inflation portion; and
   (v) stretching the multi-lumen member.

4. The method of claim 1, wherein (c) forming the main inflation portion and (d) forming the side inflation portion further comprises:
   (i) placing the multi-lumen member into a mold;
   (ii) inflating the main inflation portion and the side inflation portion; and
   (iii) stretching the multi-lumen member.

5. The method of claim 1, wherein (a) extruding the multi-lumen member further comprises extruding the multi-lumen member using a polymeric material.

6. The method of claim 1, further comprising:
   (e) coupling the dual balloon system to the catheter assembly so that the main inflation portion is positioned to expand a stent carried by the catheter system, and the side inflation portion is positioned to expand an expandable structure of the stent.

7. The method of claim 1, wherein separating the middle portion of the side tube from the main tube at the joined portion comprises cutting the middle portion of the side tube from the main tube using a knife.

8. The method of claim 1, wherein separating the middle portion of the side tube from the main tube at the joined portion comprises cutting the middle portion of the side tube from the main tube using a laser.

9. The method of claim 1, wherein separating the middle portion of the side tube from the main tube at the joined portion comprises breaking the middle portion of the side tube away from the main tube.

10. A method of forming a dual balloon system for a catheter assembly for deployment in a bifurcated vessel, the method comprising:
   (a) extruding a multi-lumen member including a main tube and a side tube that are joined at a portion to form an integrated unit, the main tube defining a main lumen, and the side tube defining a side lumen;
   (b) separating a distal portion of the side tube from the main tube at the joined portion;
   (c) forming a main inflation portion in the main tube;
   (d) forming a side inflation portion in the side tube, wherein the side tube extends along at least a first length of the main tube proximal of the main inflation portion and along at least a second length of the main tube distal of the main inflation portion; and
   (e) once the formation of the main and side inflation portions is complete, the method further comprises bonding the main and side tubes to a catheter shaft.

* * * * *